United States Patent [19]

Nakanishi

[11] Patent Number: 4,685,178
[45] Date of Patent: Aug. 11, 1987

[54] TAMPON-FORMING DEVICE
[75] Inventor: Takashi Nakanishi, Utsunomiya, Japan
[73] Assignee: Kao Corporation, Tokyo, Japan
[21] Appl. No.: 893,017
[22] Filed: Aug. 4, 1986

Related U.S. Application Data

[63] Continuation-in-part of Ser. No. 698,707, Feb. 6, 1985, abandoned.

[30] Foreign Application Priority Data

Feb. 15, 1984 [JP] Japan .................. 59-26707

[51] Int. Cl.⁴ ............................................. A61F 13/20
[52] U.S. Cl. ...................................................... 28/118
[58] Field of Search ........................... 28/118, 119, 120

[56] References Cited

U.S. PATENT DOCUMENTS

| | | | |
|---|---|---|---|
| 2,263,909 | 11/1941 | Webb | 28/120 |
| 2,286,817 | 6/1942 | Knight | 28/120 X |
| 2,566,190 | 8/1951 | Greiner et al. | 28/118 |
| 3,465,390 | 9/1969 | Mooney | 28/119 |
| 3,606,643 | 9/1971 | Mooney | 28/119 |
| 4,109,354 | 8/1978 | Ronc | 28/119 |

FOREIGN PATENT DOCUMENTS

| | | |
|---|---|---|
| 951037 | 4/1949 | France . |
| 2063263 | 7/1971 | France . |
| 2312364 | 12/1976 | France . |
| 522344 | 6/1940 | United Kingdom . |

Primary Examiner—Robert R. Mackey
Attorney, Agent, or Firm—Flynn, Thiel, Boutell & Tanis

[57] ABSTRACT

A device for forming a tampon comprising an inlet guide for a starting tampon material having an inlet opening and an outlet opening, the inlet opening being greater in the inner diameter than the outlet opening and the inlet guide having a plurality of grooves for preshaping and guiding the tampon material, a plurality of press plates disposed under the inlet guide and a plurality of fixed guide members, each of the guide members being inserted between two adjacent press plates.

12 Claims, 8 Drawing Figures

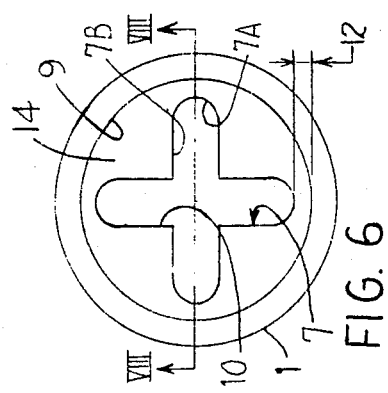
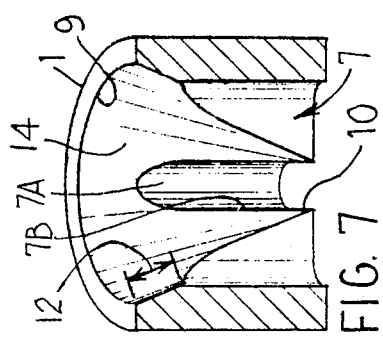
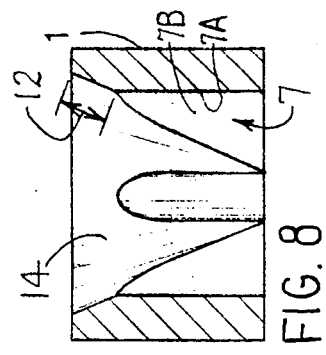
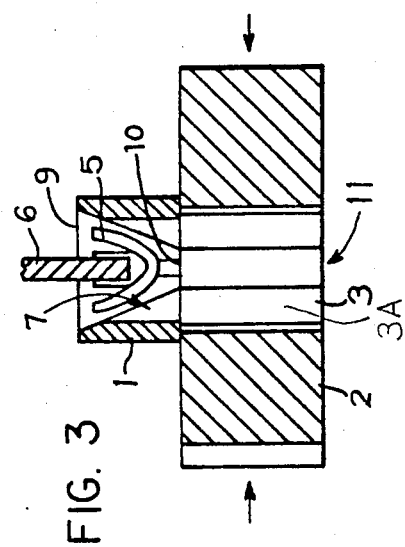
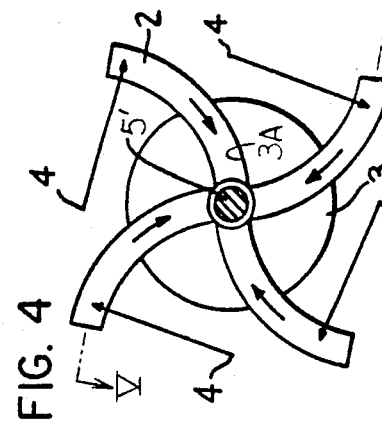
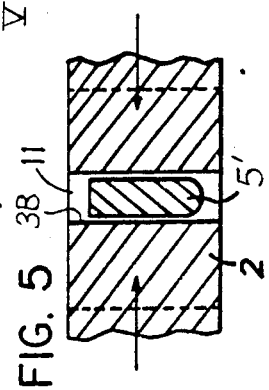
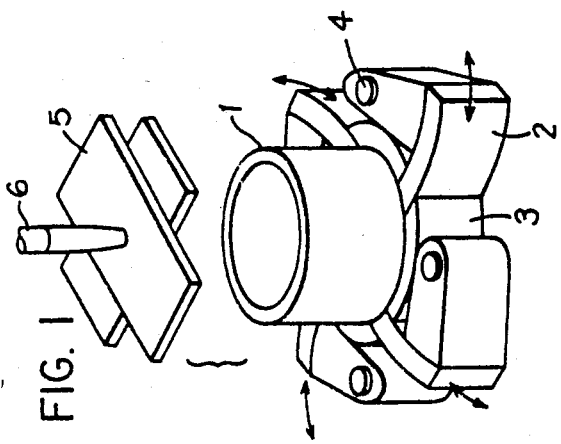
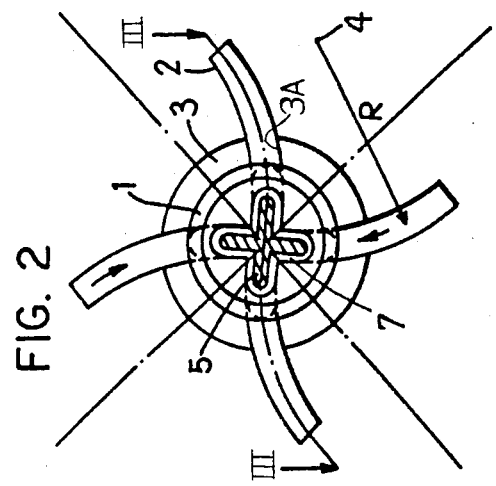

TAMPON-FORMING DEVICE

This application is a continuation in part of U.S. application Ser. No. 698 707, filed Feb. 6, 1985 now abandoned.

FIELD OF THE INVENTION

The present invention relates to a tampon forming device.

BACKGROUND OF THE INVENTION

An example of a tampon forming device is disclosed in Japanese Patent Laid-Open No. 145194/1976. This known device is a compressive forming apparatus making use of a cylindrically rolled material, and is composed of a plurality of movable guides and a plurality of press plates.

In this known tampon forming device, the supply of the cylindrical material requires that not only the press plates but also the guides move circumferentially. In consequence, spaces are formed between the guides and the press plates so that dust and small pieces of fibers of the material are inconveniently trapped and caught by these spaces. In the compression stroke of the device, the dust contaminates the product tampon and increases the friction on the guides and the press plates so as to resist the movement of these members.

The present inventor has made an intensive study to obviate the above-described problem of the known tamponforming device and has developed the present invention.

According to the invention, there is provided a tampon forming device comprising: a material inlet guide having an inlet opening and an outlet opening, the inlet opening being of greater size than the outlet opening; a plurality of press plates disposed under the inlet guide; and stationary guide members disposed between adjacent press plates. The material inlet guide also has a plurality of radial guide grooves on the inner surface thereof for preshaping and guiding tampon material to be compressed into proximity with the press plates.

BRIEF DESCRIPTION OF THE DRAWINGS

FIG. 1 is a perspective view of an embodiment of the device in accordance with the invention;

FIG. 2 is a plan view of the device in the state immediately after the driving of a tampon material;

FIG. 3 is a central sectional view taken along line III—III of FIG. 2;

FIG. 4 is a plan view of the device in the state of compressing and compacting the tampon material and with the inlet guide removed to show more clearly the structure therebeneath;

FIG. 5 is a fragmentary central sectional view taken along line V—V of FIG. 4;

FIG. 6 is an enlarged plan view of the inlet guide of FIG. 1, showing details of the radial guides;

FIG. 7 is a perspective view of the inlet guide of FIG. 6, broken away in central-section along line VIII—VIII of FIG. 6; and FIG. 8 is a central sectional view taken at line VIII—VIII of FIG. 6.

DETAILED DESCRIPTION

The invention will be described more fully hereinafter with reference to the accompanying drawings.

The tampon forming device of the invention has a material inlet guide 1 located atop press plates 2 and stationary guides 3.

The central passage 14 of the material inlet guide 1 can have any desired axial cross-sectional shape, such as conical, curvilinear, flared, polygonal and so forth, provided that it has an inlet opening 9 larger in diameter than its outlet opening 10 and its diameter decreases axially therealong from inlet opening 9 to outlet opening 10. The inlet guide central passage 14 is provided on the inner surface thereof with plural radial guides 7. The radial guides 7 are formed as axially extending, circumferentially spaced apart channel-like grooves indenting the inner surface of the central passage 14 which together give the outlet opening 10 a star-shaped (here four pronged, or cruciform) configuration. The star-shaped outlet 10 opening is to preshape the tampon material as it is driven therethrough into a tampon forming space 11 between the press plates 2 below. Each press plate 2 is adapted to be moved along an arcuate path having a radius R and centered at a press pivot point 4 (FIGS. 2 and 4). Each pair of stationary guides 3 guides therebetween a corresponding press plate 2. Although the preferred embodiment employs four press plates, four stationary guides, and four radial guide grooves, these numbers are not exclusive.

The particular inlet guide 1 depicted in detail in FIGS. 3, 6, 7 and 8 has a conical central passage 14 whose inner wall surface extends linearly between the inlet opening and outlet opening. To aid in the insertion of tampon material into the inlet guide the radial guides may be formed to extend less than the entire length of the inlet guide, thereby leaving an ungrooved area 12 of inner wall surface near the inlet opening 9. It is preferred that the radial guide grooves 7 extend to a location in the inlet guide where the bottom of the groove meets the inner surface of the inlet guide 1, as the diameter of the central passage 14 increases with the distance from the outlet opening 10. This ungrooved area 12 in the embodiment shown is an extension of the conical surface of the inner wall of the inlet guide 1. In the embodiment shown in FIGS. 6 and 7, the radial guide grooves 7 have a rounded (here semi-circular) bottom 7A connecting planar parallel sidewalls 7B, thereby giving the groove 7 a U-shaped cross-section. The bottom 7A extends substantially parallel with the axes of the central passage 14.

Circumferentially alternating press plates 2 and stationary guides 3 therefor define a final tampon forming unit 2, 3 directly coaxially underlying the material inlet guide 1.

Each press plate 2 is adapted to be moved along an arcuate path having a radius R and centered at a press pivot point 4 (FIGS. 2 and 4). Each pair of stationary guides 3 guides therebetween a corresponding press plate 2. Although the preferred embodiment employs four press plates, four stationary guides, and four radial guide grooves, these numbers are not exclusive.

The circumferential arrangement of press plate receiving spaces 3A between stationary guides 3 is the same as that of the radial guide grooves 7. The spaces 3A intersect and together form the tampon forming space 11. The radially inner part of each space 3A is axially aligned with a corresponding radial guide groove 7, and is of circumferential width and radial extent similar to and not less than the radial width and radial extent (with the press plates retracted outwardly as in FIG. 2) of the spaces 3A. Thus, material pressed down through the grooves 7 will continue smoothly into the central portion of spaces 3A. The circumferential distribution of spaces 3A and grooves 7 is preferably even.

To form a tampon with the device of the invention, the press plates 2 are first displaced radially outwardly as shown in FIG. 2. Then, two transversely crossed strips of tampon forming material 5 are located over the inlet guide 1 and are driven downwardly therethrough by a driving rod 6 into the final tampon forming unit 2, 3. As the tampon material is driven downward through the inlet guide 1, some of the tampon material is forced by the convergence of the central passage 14 into the radial guide grooves 7, thereby preforming the tampon material into a generally cruciform shape in the embodiment shown. This cruciform shape of the thus initially formed tampon material 5 can be seen in FIG. 2. The arms of the cruciform tampon material are aligned axially with respective press plate spaces 3A of the final forming unit 2, 3, facilitating receipt into the latter of the projecting arms of the cruciform tampon material 5. The cruciform tampon material 5 thus is driven down into the device final forming unit 2, 3. Then the material is radially compressed and compacted into cylindrical form in the central tampon forming space 3B by movement of the press plates towards the center of the unit 2, 3, thus becoming the tampon absorber 5' illustrated.

In this tampon forming device, since the stationary guides 3 are not movable, a constant clearance is maintained between the stationary guides 3 and the press plates 2 to prevent fiber dust and so forth from coming into the such clearance, thereby ensuring smooth movement of the movable parts relative to the stationary parts and, hence, ensuring a high durability of the device.

What I claim:

1. A machine for manufacturing tampons, comprising: a plurality of stationary guide members arranged in a circular array around a central axis, the radially inner sides of said guide members being radially spaced from the central axis to define a tampon-forming zone therebetween, said zone being open at one end thereof, adjacent ones of said guide members having complementary curved side surfaces disposed in opposed circumferentially spaced relation to one another so as to define uniform, substantially radially extending, arcuate channels between said guide members, which channels converge toward the central axis; a plurality of arcuate press plates having pressing ends for forming a tampon by compression, said press plates being movably disposed in said channels for simultaneous pivotal movement about axes that are parallel with said central axis and in directions toward and away from said central axis for compressing material in said zone to form a tampon; means defining an inlet guide tube extending axially toward said one end of said tampon-forming zone for preforming tampon material to a substantially star-shaped cross-section and introducing said star-shaped cross-section tampon material into said zone for compression between said press plates, the internal diameter of said guide tube decreasing in a direction toward said zone, the inner wall of said guide tube having axially extending, circumferentially spaced apart grooves adapted for preforming said tampon material, said grooves being substantially axially aligned with the pressing ends of said press plates, wherein the grooves impart the inside of said inlet guide tube with said substantially star-shape in the region immediately above said tampon-forming zone; and a driving member for moving tampon material axially through said inlet guide tube into said zone between said press plates, each of said press plates remaining in constant contact with at least a portion of both of its associated complementary curved surfaces of said stationary guide members as said press plates move toward and away from said tampon-forming zone.

2. A machine as claimed in claim 1, wherein said grooves extend axailly from the tampon-forming zone to a line axially spaced a predetermined distance from said zone, the part of said guide tube remote from said zone being without grooves.

3. A machine as claimed in claim 2, wherein said line is disposed where the bottoms of said grooves meet the surface of the inner wall of said guide tube as the internal diameter of said guide tube increases away from said tampon-forming zone.

4. A machine as claimed in claim 1, wherein each of said grooves has a bottom which extends parallel to said central axis of said machine.

5. A machine as claimed in claim 4, in which said press plates are arcuate plates and including pivot means supporting said press plates for movement through an arc of constant radius.

6. A machine as claimed in claim 4, wherein said driving member comprises a driving rod for moving tampon material axially through said inlet guide tube and between said press plates.

7. A machine as claimed in claim 1, wherein said grooves are U-shaped in cross-section.

8. A machine as claimed in claim 7, in which the inner end of said inlet guide tube contacts corresponding adjacent ends of said guide members and closes said one end of said tampon-forming zone.

9. A machine as claimed in claim 1, wherein said grooves and press plates are each four in number and are evenly circumferentially distributed.

10. A machine as claimed in claim 1, in which said inner wall of said inlet guide tube is a surface of revolution of radius decreasing toward said zone, said grooves indenting said surface of revolution, said grooves meeting circumferentially at the bottom of said inlet guide tube such that the decreasing radius inner wall of said inlet guide tube is essentially entirely obliterated by said grooves therein, the radial depth of said grooves increasing axially toward said zone.

11. A machine for manufacturing tampons, comprising: a plurality if stationary guide members arranged in a circular array around a central axis, the radially inner sides of said guide members being radially spaced from the central axis to define a tampon-forming zone therebetween, said zone being open at one end thereof, adjacent ones of said guide members having complementary curved side surfaces disposed in opposed circumferentially spaced relation to one another so as to define uniform, substantially radially extending, arcuate channels between said guide members, which channels converge toward the central axis; a plurality of arcuate press plates having pressing ends for forming a tampon by compression, said press plates being movably disposed in said channels for simultaneous pivotal movement about axes that are parallel with said central axis in directions toward and away from said central axis for compressing material in said zone to form a tampon, an inlet guide tube extending axially away from said one end of said tampon-forming zone for introducing tampon material into said zone for compression between said press plates, the internal diameter of said guide tube decreasing in a direction toward said zone, the inner wall of said guide tube having indented axially extending, radially spaced apart grooves adapted for preforming said tampon material, said grooves being disposed in substantial axial alignment with the pressing ends of said press plates, and having U-shaped bottoms parallel to said central axis of said machine, wherein the grooves extend axially toward the tampon-forming zone from a line axially spaced a predetermined distance from said zone, said line being disposed where said bottom of said grooves meets the surface of the inner wall of said guide tube as the internal diameter of said guide tube increases in the direction away from said zone.

12. A machine as claimed in claim 9, wherein the inner wall of said guide tube is conically shaped.

* * * * *

UNITED STATES PATENT AND TRADEMARK OFFICE
CERTIFICATE OF CORRECTION

PATENT NO. : 4 685 178

DATED : August 11, 1987

INVENTOR(S) : Takashi NAKANISHI

It is certified that error appears in the above-identified patent and that said Letters Patent is hereby corrected as shown below:

Column 4, Line 49; Change "if" to ---of---.

Column 4, Line 65; Change "tampon," to ---tampon;---.

Signed and Sealed this

Twenty-ninth Day of March, 1988

*Attest:*

DONALD J. QUIGG

*Attesting Officer*      *Commissioner of Patents and Trademarks*